United States Patent [19]

Beavers

[11] Patent Number: 5,741,940
[45] Date of Patent: Apr. 21, 1998

[54] PROCESS FOR THE PRODUCTION AND PURIFICATION OF VINYL CARBONYLS

[75] Inventor: William A. Beavers, Longview, Tex.

[73] Assignee: Eastman Chemical Company, Kingsport, Tenn.

[21] Appl. No.: 671,887

[22] Filed: Jun. 28, 1996

Related U.S. Application Data

[62] Division of Ser. No. 536,317, Sep. 29, 1995, Pat. No. 5,637,774.

[51] Int. Cl.$^6$ .................................................. C07C 45/82
[52] U.S. Cl. ........................................ 568/410; 203/62
[58] Field of Search .............................. 508/410; 203/62

[56] References Cited

U.S. PATENT DOCUMENTS

| | | | |
|---|---|---|---|
| 3,228,985 | 1/1966 | Carpenter et al. | 568/410 |
| 3,701,798 | 10/1972 | Snapp et al. | 568/390 |
| 3,928,458 | 12/1975 | Hagemeyer et al. | 568/390 |
| 4,005,147 | 1/1977 | Fischer et al. | 568/390 |
| 4,476,324 | 10/1984 | Reichle | 568/390 |
| 5,004,839 | 4/1991 | Pugach et al. | 568/390 |
| 5,026,119 | 6/1991 | Dessau | 568/313 |
| 5,072,051 | 12/1991 | Pugach et al. | 568/370 |

OTHER PUBLICATIONS

F. F. Blicke; Organic Reactions, 1, 303 (1942); "The Mannich Reaction".

E. M. McMahon, et al., Journal American Chemistry Society, 70, 2971 (1948), Preparation and Properties of Ethyl Vinyl Ketone and Methyl Isopropenyl Ketone.

R. B. Woodward, et a., Journal American Chemical Society, 74, 4223 (1952), The Total Synthesis of Steroids.

B. Byrne, et al. Synth., 870 (1986), A Convenient Preparation of Ethyl Vinyl Ketone.

Japanese Patent abstract 62142135 (1987).

*Primary Examiner*—James H. Reamer
*Attorney, Agent, or Firm*—Mark A. Montgomery; Harry J. Gwinnell

[57] ABSTRACT

Disclosed is a very economical way to produce vinyl carbonyls such as ethyl vinyl ketone. Disclosed also is a purification process of separating vinyl carbonyls and coreactants. The catalyst and reaction conditions give useful yields of vinyl carbonyls, the thermodynamically unfavorable product along with coreactants that are more thermodynamically favored. Disclosed also is the separation of reactants that takes place at low distillation temperatures and pressures in the presence of antioxidant.

12 Claims, No Drawings

PROCESS FOR THE PRODUCTION AND PURIFICATION OF VINYL CARBONYLS

This is a divisional application of application Ser. No. 08/536,317, filed Sep. 29, 1995 U.S. Pat. No. 5,637,774.

FIELD OF THE INVENTION

The present invention relates to a novel process of producing vinyl carbonyls. The present invention also relates to a process of purifying vinyl carbonyls such as ethyl vinyl ketone.

BACKGROUND OF THE INVENTION

Vinyl carbonyls, such as ethyl vinyl ketone, are important starting materials for the preparation of pharmaceutical and agricultural compounds. Because of their ability to react at either their carbonyl group or unsaturated position, vinyl carbonyls form a locus for the preparation of a wide variety of herbicides, pesticides, steroids, and medicines. However, vinyl carbonyls are not extensively used because they are expensive and not widely available.

Vinyl carbonyls, specifically ethyl vinyl ketone, form as a minor constituent from the Mannich reaction of methyl carbonyls, such as methyl ethyl ketone with formaldehyde (see F. F. Blicke; Organic Reactions, 1, 303 (1942); "The Mannich Reaction"). Other aldol condensations of methyl ethyl ketone with formaldehyde also form ethyl vinyl ketone usually as a minor contaminant in methyl isopropenyl ketone (please see U.S. Pat. Nos. 3,928,458 and 5,072,051 and E. M. McMahon, et al., Journal American Chemistry Society, 70, 2971 (1948), Preparation and Properties of Ethyl Vinyl Ketone and Methyl Isopropenyl Ketone). The difference in these preparations is the use of different aldol catalysts, sources of formaldehyde, and/or reaction conditions. However, no process produces significant quantities of vinyl carbonyls. Under the conditions of these publications the reactions lead to preponderant of the methyl isoalkenyl ketone, (i.e. methyl isopropenyl ketone). Attempting to increase the temperature to favor more equal amounts of the vinyl carbonyl rarely raises the amount much because heat also promotes the degradation of the vinyl carbonyls, reduces the catalyst activity, and/or decreases the selectivity. In most cases the mixture of methyl carbonyl reaction components is not acceptable. In fact, in some processes great lengths are made to ensure that only one isomer is present to start with. The standard preparation of pure ethyl vinyl ketone is the reaction of ethylene with propionyl chloride in nitromethane catalyzed by equimolar quantities of aluminum chloride (see R. B. Woodward, et al., Journal American Chemical Society, 74, 4223 (1952), The Total Synthesis of Steroids). In this case the yield of ethyl vinyl ketone is 22 percent. An improved yield of ethyl vinyl ketone comes from a four step synthesis starting with diethyl ketone (see B. Byrne, et al. Synth., 870 (1986), A Convenient Preparation of Ethyl Vinyl Ketone). In this case the yield of ethyl vinyl ketone is 67 percent. But in both cases the reactions consume equimolar quantities of expensive coreactants and produce copious amounts of waste products. For these reasons, neither reaction is suitable for manufacturing vinyl carbonyls.

Another reason why vinyl carbonyls are not widely available due to cost is the difficulty in the purification of the reaction components. Separating vinyl carbonyls and other reaction components, such as ethyl vinyl ketone from methyl isopropyl ketone is difficult because of the similar physical and chemical properties of the reaction products and the fact that they polymerize readily, especially in the presence of heat or bases.

Likewise, vinyl carbonyls are an unacceptable contaminant with the other reaction components such as isopropenyl ketone. One way to remove small amounts of ethyl vinyl ketone from methyl isopropenyl ketone uses strong base to selectively polymerize the ethyl vinyl ketone (see Japanese Patent Abstract 62142135 (1987).

It would be very desirable to be able to economically produce vinyl carbonyls. It would also be very desirable to economically produce vinyl carbonyls in essentially pure form by the purification of a mixture of reaction components.

SUMMARY OF THE INVENTION

The process according to the present invention for producing vinyl carbonyls comprises contacting a methyl carbonyl with formaldehyde in the presence of a weakly acidic zeolite catalyst at a temperature of about 50° to 1,000° C. for a time between 0.01 to 1,000 seconds, said time varying inversely proportional to the temperature such that at 1000° C. the contacting time is nearer 0.01 seconds than 1000 seconds thereby producing vinyl carbonyl.

The present invention also further comprises a purification process for purifying the vinyl carbonyls, separating unreacted reactants and byproducts. The purification process according to the present invention entails distilling the reactants and coproducts in the presence of an antioxidant under acidic conditions at a temperature below 50° C. and a pressure below 350 mmHg such that the antioxidant (a polymerization inhibitor) is coated on all contact surfaces.

DETAILED DESCRIPTION OF THE INVENTION

The applicant has unexpectedly discovered a process for the production of vinyl carbonyls. This process is conducted at a temperature of 50° C. to 1,000° C. for a time between 0.01 to 1,000 seconds. This process is clearly unexpected since vinyl carbonyls have a tendency to polymerize even at 30° C. Thus, it is counter intuitive to expect its survival at temperatures above 50° C. to 1,000° C. particularly at above 600° C. However, temperatures approaching this level are necessary according to the present invention to promote even moderate production of the vinyl carbonyl, ethyl vinyl ketone because, at lower temperatures, the reaction has a strong preference to make other isomers (for example, methyl isopropenyl ketone). Further, catalysts which, at high temperatures can catalyze the aldol reaction of methyl ethyl ketone with formaldehyde also lose activity at high temperatures. Those same high temperatures that produce the product rapidly foul catalyst surfaces and change the chemical nature of these catalysts so that the activity rapidly drops. The catalyst and reaction conditions according to the present invention give useful yields of vinyl carbonyls, the thermodynamically unfavorable product along with methyl isoalkenyl ketones, the thermodynamically favorable product.

Separating the above coproducts is necessary for using either as a starting point for more complex derivatives. Another key feature of the present invention is the separation and purification of the coproducts, vinyl carbonyls, and methyl isoalkenyl ketone (e.g. ethyl vinyl ketone and methyl isopropenyl). This separation has proven so difficult in the past that extreme measures were made to avoid the separation. Thus, only simple flash distillations were attempted rather than the more extensive fractional distillation really necessary for a complete separation. Even at the simple distillation conditions problems occurred as stated above. The purification process according to the present invention entails distilling the reactants and coproducts in the presence of an antioxidant under acidic conditions at a temperature below 50° C. and a pressure below 350 mmHg such that the antioxidant (a polymerization inhibitor) is coated on all contact surfaces.

This means that the antioxidant or polymerization inhibitors that prevent the formation of free radicals is coated on all surfaces of the equipment that come in contact with the product.

Applicant has also unexpectedly discovered a catalyst that is very useful for the production of vinyl carbonyls. In the present invention, fouling of the present catalyst surface actually improves the catalysts activity, very different from what happens with known catalyst. Additionally, the chemical stability of the present catalyst resists change until reaching temperatures above those useful in the present reaction.

The process according to the present invention is the reaction of methyl carbonyl with formaldehyde over various molecular sieve zeolite catalysts to make vinyl carbonyls. Suitable zeolites include A type, Y type, ZSM type, and SK500. They function in their original form or in exchanged form replacing the original alkaline or alkaline earth metal ions with hydrogen ions, other alkaline or alkaline earth ions, transition metal ions, lanthanide ions, or actinide ions. Some zeolites perform better than others especially those with moderate sized cavities into which ethyl vinyl ketone can readily fit having an average cavity size of about 4 Å to 14 Å. The more preferred catalysts are the zeolites of the A type and the ZSM type, with the A type zeolites being more preferred. The most preferred A type zeolite catalysts are the 5 Å and 5 Å molecular sieves exchanged with ammonium ions and calcined to convert the ammonium ion form into the hydrogen ion form. The catalyst used in the reaction is preferably in the form of a fixed bed through which the substrate passes.

The preferred catalyst according to the present invention is acidic that has labile metal ions exchanged with hydrogen ions at 0.1 percent to 100 percent. The catalyst according to the present invention needs to be acidic, however, as the reaction occurs the reactive basic sites on the catalyst that produce products other than the desired vinyl carbonyls eventually foul over time and plug being rendered inactive thus the activity of the catalyst over time increases towards the production of vinyl carbonyls. The acidic zeolite catalyst according to the present invention is preferably more acidic and has labile metal ions exchanged with hydrogen to at least 10 percent to 100 percent.

The conditions under which the reaction occurs depends on the catalyst. Usable concentrations of the reactants methyl ethyl ketone (a preferred methyl carbonyl) and formaldehyde vary over a wide range. Methyl ethyl ketone can react at concentrations of $10^{-5}$ to 12 molar. A more preferred concentration is 0.1 to 11 molar, with the most preferred concentration being 5 to 10 molar. The reaction takes place when the ratio of methyl carbonyl to formaldehyde is 1000:1 to 1:1000, the ratio is more preferably 1000:1 to 1:1, with the most preferred ratio being 10:1 to 2:1.

The preferred methyl carbonyl is a methyl ketone that produces a vinyl ketone. As stated above a more preferred methyl carbonyl reactant to produce the vinyl carbonyl is methyl ethyl ketone. The source of methyl ethyl ketone is usually liquid methyl ethyl ketone. But any derivative of methyl ethyl ketone which changes into methyl ethyl ketone under the reaction conditions is suitable. Such derivatives include the methyl ethyl ketone ketals such as the dimethyl ketal, the diethyl ketal, the dipropyl ketal, and the dibutyl ketal and the cyclic ketals including the ethylene glycol ketal, the propylene glycol ketals, and the butylene glycol ketals. Likewise, the source of formaldehyde is usually aqueous formalin. But any source which liberates free formaldehyde under the reaction conditions is suitable. Such sources include formacels (formaldehyde in alcohol solvents), paraformaldehyde slurries, or trioxane.

In addition to these reactants, there are a number of inert diluents which can mix with these reactants without changing the reaction. Such diluents include water, hydrocarbons, and inert gases. Such diluents are important means of modifying the contact times of the reactants with the catalyst. So they can help adjust reaction parameters to optimal values.

The conditions under which the reaction takes place vary over a wide range. This wide range is what makes the reaction so versatile. The optimum values depend, to a certain extent, upon what zeolite catalyst is used. With preferred hydrogen ion modified 5 Å zeolite catalyst, the temperatures at which the reaction will take place are about 50° to 1,000° C. Below this range, the reaction still occurs, but the rate is too low to be of commercial importance. Above this range, the catalyst, reactants, and products all decompose so it is also of little commercial importance. A more preferred temperature range is 150° to 800° C., with the most preferred temperature range being 180° to 650° C. The catalyst contact times can also vary over a wide range, but these times are influenced by the reaction temperatures. These contact times vary from 0.01 to 1,000 seconds. At the lower reaction temperatures, the optimum contact times are usually higher and at the higher reaction temperatures, they are usually lower. In the more preferred temperature range, the contact times vary from about 1 to 25 seconds, with the contact times varying from about 2 to 15 seconds in the most preferred temperature range.

Pressure is not a concern to the success of this reaction. Thus any pressure within 0.001 and 1,000 atmospheres is suitable. It is understood that modifying the pressure changes the contact times of catalyst with reagents. This change may be substantial if such pressures are used which cause the phase in which the reaction occurs to change from gas to liquid or from liquid to gas. The gas phase is preferred, therefore, a more preferred pressure range is 0.1 to 100 atmospheres, with the most preferred pressure range being 1 to 10 atmospheres. The most preferred pressure range corresponds to the pressure required to push the gaseous reagents across the catalyst bed with contact times in the most preferred range and with the exit pressures at or near atmospheric.

Under the most preferred reaction conditions, the conversion of formaldehyde is usually 50 to 95 percent. Since it is usually present in much higher concentrations, the methyl ethyl ketone conversion is proportionately lower, usually 5 to 60 percent. At a methyl ethyl ketone to formaldehyde ratio of 5:1, the methyl ethyl ketone conversion is typically 7 to 18 percent.

Under the optimum conditions in the process of the present invention, the reactants and products are gases and there is a marked lightening of the product color. The applicant has also discovered that the ratio of ethyl vinyl ketone product to methyl isopropenyl ketone product also rises with the temperature. At the lower end of the most preferred temperature range, the ratio is typically 0.3 to 0.5.

At the higher end of the temperature range, the ratio is typically 0.6 to 0.8. It is believed that this increase in the ratio occurs because the higher temperature overcomes the energy difference between the intermediate leading to and favoring methyl isopropenyl ketone and the intermediate leading to ethyl vinyl ketone. At increasingly higher temperatures, the ratios approach statistical values. These intermediates appear as follows:

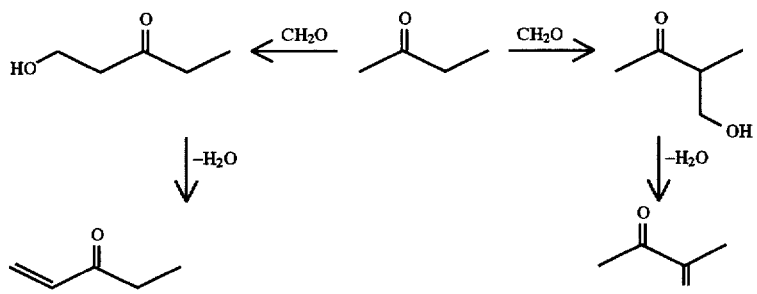

The yield of ethyl vinyl ketone is highest near the middle of the preferred temperature range. At the lower end of the range, it is lower because more of the reactant forms methyl isopropenyl ketone. At the higher end of the range, it is lower for two reasons. First, more of the product fouls the catalyst, and second, there are more byproducts. The byproducts come from methyl ethyl ketone as the increased temperatures open more pathways to side reactions and the products, ethyl vinyl ketone and methyl isopropenyl ketone. The most remarkable byproducts from ethyl vinyl ketone and methyl isopropenyl ketone at these high temperatures are their reduction products, diethyl ketone and methyl isopropyl ketone respectively. At such elevated temperatures, the zeolites have apparently become hydrogenation catalysts as well as aldol catalysts.

Another discovered remarkable feature of the zeolite catalysts is their stability for this reaction. This stability permits the reaction to take place at the high temperatures necessary to give the best yields of ethyl vinyl ketone. The stability also permits complete or nearly complete reconditioning of the catalysts simply by calcining at 650° to 850° C. in air for 2 to 6 hours.

Unrelated to this stability but important to the extended use of the catalyst is the fact that fouling of the catalyst is slow. Reaction at 450° C. for 3 weeks showed a 35 percent decline in the catalyst activity. Accompanying this decline in activity, the selectivity to ethyl vinyl ketone improved 10 percent. The fouling was apparently removing sites leading to byproducts faster than it was removing sites leading to ethyl vinyl ketone. After reconditioning, this catalyst returned to 95 percent of its initial activity. Regeneration or reconditioning of the catalyst is preferably done in an oxygen containing gas such as air at 400° C. to 1200° C.

The process according to the present invention for the separation of vinyl carbonyls from methyl isoalkenyl ketones comprises:

(a) fractionally distilling a mixture of vinyl carbonyl, methyl isoalkenyl ketone, and unreacted reactants, methyl carbonyl and formaldehyde, at a temperature below 50° C. and a pressure below 350 mmHg to remove methyl carbonyl;

(b) steam distilling at a water to distillant ratio of 1:1 to 3:1, a temperature below 100° C., and a pressure no greater than 760 mmHg to remove formaldehyde;

(c) azeotropically drying in the presence of antioxidant, at a temperature of 10° C. to 60° C. and a pressure of 5 mmHg to 150 mmHg to remove water; and (d) fractionally distilling under acidic conditions, in the presence of antioxidant, at a temperature of about −10° C. to 40° C. and a pressure of 0.1 mmHg to 50 mmHg, to remove methyl isoalkenyl ketone thereby recovering vinyl carbonyl.

If the physical separation of vinyl carbonyls from coreactants were possible, it would obviate the expensive preparation of pure reactants such as the vinyl carbonyls and coreactants methyl isoalkenyl ketones. However, separation by fractional distillation is difficult for several reasons. First, the boiling point difference of coreactants at one atmosphere is only 4° C. Fortunately, for the present invention this difference increases to 8° C. at 10 mmHg pressure. Next, the uninhibited pure monomers polymerize at temperatures as low as 30° C. Therefore, long residence times in a distillation column, such as one would have in a fractional distillation with a high reflux ratio, lead to unacceptable column clogging and product loss by polymer formation. Finally, several distillations are necessary to complete the purification. Removing unreacted vinyl carbonyls, unreacted formaldehyde, and water each require a separate, although not difficult, distillation.

The purification process according to the present invention is also very unique. The separation of products from starting materials requires a series of fractional distillations. The first distillation removes unreacted methyl carbonyl (e.g. methyl ethyl ketone) for recycling to the aldol reactor. The second is an extractive distillation using water as the extractant to remove unreacted formaldehyde. The third distillation removes the water from the products. And the fourth distillation separates vinyl carbonyl from methyl isoalkenyl ketone (when the methyl carbonyl is the preferred, methyl ethyl ketone, then the vinyl carbonyl is ethyl vinyl ketone and the methyl isoalkenyl ketone is methyl isopropenyl ketone). A fifth distillation separates pure vinyl carbonyl from high boiling material.

The first distillation (a) takes place below 50° C., preferably below 35° C., and below 350 mmHg pressure, preferably below 200 mmHg, with a pressure of about 100 mmHg being most preferred. The critical separation is methyl ethyl ketone from methyl isopropenyl ketone, a difference of about 15° C. However, even if the separation is not complete, whatever products distill readily recycle to the aldol reactor.

The second extractive distillation, steam distilling Step (b), takes place below 100° C. and below 760 mmHg pressure, preferably below 200 mmHg, with a pressure of about 100 mmHg being most preferred. This step removes unreacted formaldehyde. Fresh water, introduced at the top of the column, runs countercurrent to the organic, introduced at the middle of the column, in a 1:1 to 3:1 ratio. The temperature in the distillation head most preferably never exceeds 45° C. For these distillations lower pressures are preferred, as low as practical. However, near a perfect vacuum is not practical because vapor densities become so low that the times to establish the required distillation equilibria are too long, thus a pressure of about 100 mmHg is best.

In the first and second distillations, the presence of formaldehyde acts as an effective radical scavenger/ antioxidant. So there is no need for additional protection against polymerization of the products. But having removed nearly all formaldehyde in the second distillation, stopping unwanted free radical polymerization of the products is possible only by adding an antioxidant, such as the hydroxylic aromatic hydroquinone or t-butyl catechol, for all subsequent steps. In the event that any base exists as a nucleating site for base promoted polymerization, adding acetic acid ensures removal of those sites. Other aliphatic or aromatic carboxylic acids, such as propionic acid can also be used.

Mixing the distillate from the extractive distillation immediately with 2 volumes of dibutyl ether 0.01 molar in hydroquinone or t-butyl catechol and 0.001 molar in butyric acid provides polymerization protection. It also helps precipitate some of the water. Removing that precipitated water in a decanter before going to the next column helps cut down the load on that column. This is important because keeping the residence time in the distillation columns to a minimum helps keep the probabilities of polymerization on the column to a minimum too. Any high boiling ether, aromatic, or aliphatic hydrocarbon can be used in the place of dibutyl ether.

Adding the decanted organic solution to the middle of the dehydration column operated at 100 mmHg pressure provides polymerization protection for the lower half of the distillation column during Step (c). Keeping the top of the column free of polymerization requires adding a constant small flow of a 1 molar solution of the antioxidant hydroquinone, and 0.1 molar butyric acid in dibutyl ether to the reflux column. This higher concentration of polymerization inhibitors keeps the volume of the countercurrent flow small thereby cutting down on any extractive distillation efforts. This treatment protects virtually all surfaces wetted by the distillate. Otherwise, the column is identical to other 20 plate fractionation columns used for dehydrations. The concentrations of the antioxidant in the column is lower than what is introduced. Much more can be added, however, this simply wastes material since only a minor amount is needed in the column. This amount can be as low as $10^{-6}$ molar in the condensed material on the column wall.

The azeotropically drying, conducted in Step (c) according to the present invention, is conducted in the presence of an antioxidant at a temperature of about 0° C. to 60° C. and a pressure of about 5 mmHg to 150 mmHg to remove water. This temperature is preferably about 20° to 40° C., with a temperature of about 30° C. being most preferred. This pressure is preferably about 10 to 100 mmHg with about 15 mmHg being most preferred.

The fractional distilling of (d) is conducted under acidic conditions in the presence of antioxidants at a temperature about −10° C. to 40° C. and a pressure of 0.1 mmHg to 50 mmHg, to remove isoalkenyl ketone thereby recovering vinyl carbonyl. This temperature is preferably about 0° C. to 30° C., with a temperature of about 25° C. being most preferred. This pressure is preferably about 3 to 40 mmHg, with about 10 to 15 mmHg being most preferred.

The distillate from the dehydration column contains a mixture of methyl isopropenyl ketone, ethyl vinyl ketone, water, and polymerization inhibitors. After separating the water in a decanter, the organic returns to the middle of the distillation column. The water from this decanter and the prefeed decanter (pre-dehydration column decanter) returns to the formaldehyde extractive distillation column to recover any ethyl vinyl ketone and methyl isopropenyl ketone values. Dry product in inhibited dibutyl ether overflows the base of the dehydration column into the feed tank for the final purification column.

The important separation column, Step (d), is like the dehydration column except that it is larger and operates at lower pressures. The column is preferably 40 plates or more than 40 plates and operates at about 10 mmHg pressure. Feeding the dry overflow from the base of the dehydration column to the middle of this column with the 1 molar hydroquinone and 0.1 molar butyric acid inhibitor solution added to the top of the column at the reflux condenser permits separation of the methyl isopropenyl ketone from the ethyl vinyl ketone with no polymerization on the distillation column. The methyl isopropenyl ketone distills overhead and adding at least 0.001 molar hydroquinone immediately to this distillate ensures arresting any incipient polymerization. The ethyl vinyl ketone along with dibutyl ether and the polymerization inhibitors exit through the column base.

Recovering pure ethyl vinyl ketone from the product mixture requires an additional Step (e) to remove the product from the high boiler, dibutyl ether. The product, ethyl vinyl ketone, is removed from this base material from the last purification column through a short column. The only separation needed in this column is ethyl vinyl ketone from dibutyl ether, a boiling point difference of about 30° C. to 50° C., depending on the pressure. Treating the column with the hydroquinone/butyric acid solution ensures arresting any possible polymerization. It is important to keep in the boiling and receiving pot a concentration of at least 0.001 molar hydroquinone in the product at all times to ensure arresting any incipient polymerization.

The final separation is the separation of the dibutyl ether from the base of this last column for recycling to the ethyl vinyl ketone/methyl isopropenyl ketone separation and purification columns. This distillation usually takes place under vacuum; however, the vacuum separation is not necessary. Rather, it is merely convenient to keep the base temperatures from exceeding the decomposition temperatures of the residual compounds. Little of the residual compounds codistills with the dibutyl ether even though this is not necessarily a fractional distillation. So treating the distillate with fresh hydroquinone and butyric acid is important to bring their concentrations up to the levels needed for arresting polymerization in the product streams.

The following examples are intended to illustrate the present invention but are not intended to limit the reasonable scope thereof.

EXAMPLES

Example 1

While stirring, 201 grams of commercial 5A Molecular Sieves (identified as 5 Å Linde molecular sieves from Union Carbide Corporation) were slowly charged into a solution of 20.4 grams ammonium chloride dissolved in 250 milliliters water to start the exchange of calcium ions with ammonium ions. After complete addition, the temperature of the water had climbed to 60° C. The mixture was allowed to stand for one hour with occasional stirring to continue the exchange. After one hour, the solution was filtered away from the residue to complete the treatment. Treating this residue was then conducted with a fresh batch of 20.3 grams ammonium chloride in 250 milliliters of water to ensure as complete exchange as possible. The ammonium chloride solution was filtered away and the filtered residue was washed with 3×200 milliliter portions of distilled water to remove the residual ammonium chloride. After filtering away the excess water, the residue was exposed to a stream of dry nitrogen to remove the rest of the water.

The treated dried molecular sieves were heated in a porcelain dish to 750° C. for one hour and converted into the protonic form. At 600° C. the solid began emitting ammonia gas. This emission had stopped by the time the solid had reached its final temperature. Upon reaching room temperature, it was ready for charging into the hot tube reactor.

This example above illustrates the method for the preparation of a special catalyst according to the present invention.

Example 2
Pelletizing Powdered Catalyst

Powdered catalyst was not suitable for evaluation in the hot tube reactor. So every powdered catalyst was formed into cylindrical pellets ½" in diameter and ³⁄₁₆" thick using a press. Thus, mixing 71.3 grams of VALFOR CBV-8020 (HZSM-5 zeolite with Si:Al ratio 80:1 from the PQ Corporation), 3.3 grams starch powder, and 0.4 grams paraffin provided the stock to be formed into these pellets. The purpose of the starch was to add porosity to the final pellet and the purpose of the paraffin was to provide lubrication for the pellet press. Each pellet contained 500 to 530 milligrams of the stock mixture. After forming all of the mixture into pellets, calcining them at 750° C. for two hours in air introduced about 5 percent porosity by burning off the starch and paraffin components. After completing the calcining, the pellets were too large to fit into the hot tube reactor. So cutting each pellet into eights provided pieces suitable for filling the reactor.

The purpose of this example was to show the method of converting undesirable powdered catalyst into usable catalyst pellets.

Example 3

The only preparation of catalyst for the general run was charging 75 cubic centimeters of the catalyst into the hot tube reactor and sealing the reactor. Maintaining a 180 to 230 cubic centimeter per minute nitrogen flow over the catalyst during the course of the experiment usually occurred. But the flow only adjusted the contact time of the reagents with catalyst and was not necessary for the success of the reaction. In this particular experimental set, the catalyst was the one described in Example 1.

The reagents for the reaction typically consisted of a solution of 630.0 grams of methyl ethyl ketone (8.737 moles) and 141.8 grams of 37 percent aqueous formalin (1.747 moles). The molar ratio of methyl ethyl ketone to formaldehyde was 5.00:1 and the solution contained 81.6 weight percent methyl ethyl ketone, 6.8 weight percent formaldehyde, and 11.6 weight percent water. The density of this solution was 0.846 grams per cubic centimeter and the feed rate was 0.4 to 0.7 cubic centimeter per minute.

Reaction temperatures varied systematically from 150° to 750° C. Under these conditions, the contact times of the reagents with the catalyst ranged from 4.2 to 12.8 seconds depending on the temperature, the feed rate, and the nitrogen flow rate. The product exiting the reactor condensed in a series of heat exchangers and collected in a reservoir. Analyzing samples from the reservoir provided a profile of the conditions under which the reaction would succeed. This profile defined the suitability of the catalyst. For the present catalyst, the highly successful range was 330° to 710° C. At 330° C the yield of ethyl vinyl ketone was 23.4 percent and at 710° C. the yield of ethyl vinyl ketone was 41.0 percent. The coproduct yields at 330° C. were 69.5 percent methyl isopropenyl ketone and at 710° C. were 36.2 percent methyl isopropenyl ketone, 2.2 percent methyl isopropyl ketone, and 3.3 percent diethyl ketone. Below 540° C. the yield of methyl isopropyl ketone and diethyl ketone was negligible.

The purpose of this example was twofold. First, it showed the general method used for all preparative runs. And second, it showed the results of the run using the protonic 5 Å (H5 Å) molecular sieve catalyst prepared in Example 1 in particular.

Example 4

Repeating example 3 using the pelletized HZSM-5 zeolite catalyst from Example 2 instead of the H5 Å molecular sieve catalyst from Example 1 gave the following results: The highly successful range was 320° to 450° C. But it took the catalyst several hours of operation before it began producing any product at all. This result was presumably because it took the catalyst that long to change into its final active form or it took that long for carbon buildup to quell the hyperactive sites.

At 320° C. the yield of ethyl vinyl ketone was 12.6 percent on 86.6 percent formaldehyde conversion and at 450° C. the yield was 32.2 percent on 99.2 percent formaldehyde conversion. At these same temperatures, the yield of the coproduct methyl isopropenyl ketone was 37.5 percent and 44.1 percent respectively.

The purpose of this example was to show the results of the aldol condensation with another zeolite catalyst.

Example 5

Repeating Example 4 using the same catalyst for 3 weeks at 395° to 405° C. gave the following results: The yield of ethyl vinyl ketone throughout this time span improved from 24.5 percent on 85.8 percent formaldehyde conversion initially to 38.2 percent on 81.1 percent formaldehyde conversion at the end. During this same time, the yield of the coproduct methyl isopropenyl ketone improved from 35.9 percent initially to 47.6 percent at the end. At the end of this experiment the catalyst activity had not declined detectably.

The purpose of this experiment was to gauge the extended activity of the zeolite catalysts.

Example 6

Recovering the catalyst from Example 5 showed the initially pure white catalyst to be covered with a layer of carbon. Calcining this recovered catalyst at 750° C. in air for 2 hours completely removed the carbon coating restoring it to its original pure white color. The activity of this catalyst on reintroduction into the hot tube reactor was the same as that of fresh catalyst.

The purpose of this example was to show how readily one can recondition the zeolite catalysts.

Example 7

Repeating Example 3 substituting SK500 zeolite catalyst (a Y type zeolite having the cations exchanged with rare earth metals from Union Carbide Corporation) for the molecular sieve catalyst gave the following results: The highly successful range was 400° to 690° C. At 400° C. the yield of ethyl vinyl ketone was 26.0 percent on 22.6 percent formaldehyde conversion and 690° C. it was 20.8 percent on 95.9 percent formaldehyde conversion. The optimum temperature was 500° C. at which point the ethyl vinyl ketone yield was 33.3 percent on 70.6 percent formaldehyde conversion. The yield of the coproduct methyl isopropenyl ketone was 31.2 percent at 400° C., 36.7 percent at 500° C., and 27.8 percent at 625° C. The formaldehyde conversion was 22.6 percent at 400° C. climbing to 95.6 percent at 625° C.

The purpose of this experiment was to show the success of another type of zeolite catalyst for the production of ethyl vinyl ketone from methyl ethyl ketone and formaldehyde.

Example 8

Repeating Example 7 substituting anhydrous trioxane for 37 percent aqueous formalin gave 27.8 percent ethyl vinyl ketone, 28.8 percent methyl isopropenyl ketone, 4.4 percent diethyl ketone, and 3.4 percent methyl isopropyl ketone at 575° C. The analysis showed a trioxane conversion of 97.7 percent. The residual free formaldehyde in the sample was 4.5 molar percent of the original based on the conversion of trioxane into three moles of formaldehyde.

The purpose of this experiment was to show the results of alternative sources of formaldehyde.

Example 9

Repeating Example 3 substituting 3–9 mesh grade 41 silica gel (Grade 57 silica Gd from Davidson Chemical) in place of the molecular sieve catalyst gave the following results: The highly successful range was 360° to 625° C. At 360° C. the yield of ethyl vinyl ketone was 12.9 percent on 74.4 percent formaldehyde conversion and at 625° C. the yield was 15.0 percent on 74.6 percent formaldehyde conversion. At 360° C. the yield of the coproduct methyl isopropenyl ketone was 57.0 percent and at 625° C. it was 22.0 percent. The low yields at the high temperatures resulted because the methyl ethyl ketone began to autocondense into a variety of byproducts. The onset of this autocondensation was 390° C. Adding to the low yields was the production of the reduction compounds, diethyl ketone and methyl isopropyl ketone. The onset of this reduction was 470° C. And at 625° C., the yield of diethyl ketone and methyl isopropyl ketone was 2.8 percent and 2.6 percent respectively.

Beside the low product yields, the activity of the silica gel began to subside after 4 days at 400° C. The formaldehyde conversion declined from 76.0 percent initially to 52.8 percent after the fourth day. Attempted regeneration of the catalyst by calcining at 750° C. for 2 hours in air failed giving fractured material resembling sand as the product.

The purpose of this experiment was to compare the results of the prior art catalyst with the catalysts of the present invention. Not only was the yield of ethyl vinyl ketone one half to two thirds lower than the best examples of the present invention, but the activity fell off at least ten times faster and the catalyst regeneration failed.

I claim:

1. A process for the separation of vinyl carbonyl from methyl isoalkenyl ketones comprising:
    (a) fractionally distilling a mixture of vinyl carbonyl, methyl isoalkenyl kentone, and unreacted reactants, methyl carbonyl and formaldehyde, at a temperature below 50° C. and a pressure below 35 mmHg to remove methyl carbonyl;
    (b) steam distilling at a water to distillant ratio of 1:1 to 3:1, a temperature below 100° C., and a pressure no greater than 760 mmHg to remove formaldehyde;
    (c) azeotropically drying in the presence of antioxidant, at a temperature of 10° C. to 60° C. and a pressure of 5 mmHg to 150 mmHg to remove water; and
    (d) fractionally distilling under acidic conditions, in the presence of antioxidant, at a temperature of about −10° C. to 40° C. and a pressure of 0.1 mmHg to 50 mmHg, to remove methyl isoalkenyl ketone thereby recovering vinyl carbonyl.

2. The process according to claim 1 wherein the distilling of step (c) is conducted in the presence of a non-refluxing solvent and said solvent is removed after step (d) by flashing.

3. The process according to claim 1 wherein said methyl carbonyl is a methyl kentone and said vinyl carbonyl is vinyl ketone.

4. The process according to claim 3 wherein said methyl ketone is methyl ethyl kentone and said vinyl kentone is ethyl vinyl kentone.

5. A process for the preparation and separation of vinyl carbonyls from methyl isoalkenyl ketones comprising:
    producing vinyl carbonyl by the process comprising contacting a methyl carbonyl with formaldehyde in the presence of an acidic zeolite catalyst at a temperature of about 50° to 1,000° C. for a time between 0.01 to 1,000 seconds, said time varying inversely proportional to the temperature such that at 1,000° C. the contacting time is nearer 0.01 seconds than 1,000 seconds thereby producing vinyl carbonyl;
    (a) fractionally distilling a mixture of vinyl carbonyl methyl isoalkenyl ketone, and unreacted reactants, methyl carbonyl and formaldehyde, at a temperature below 50° C. and a pressure below 350 mmHg to remove methyl carbonyl;
    (b) steam distilling at a water to distillant ratio of 1:1 to 3:1, a temperature below 100° C., and a pressure no greater than 760 mmHg to remove formaldehyde;
    (c) azeotropically drying in the presence of antioxidant, at a temperature of 10° C. to 60° C. and a pressure of 5 mmHg to 150 mmHg to remove water; and
    (d) fractionally distilling under acidic conditions, in the presence of antioxidant, at a temperature of about −10° C. to 40° C. and a pressure of 0.1 mmHg to 50 mmHg, to remove methyl isoalkenyl ketone thereby recovering vinyl carbonyl.

6. The process according to claim 5 wherein said zeolite catalyst has an average cavity size of about 4 Å to 14 Å.

7. The process according to claim 5 wherein said methyl carbonyl is a methyl ketone and said vinyl carbonyl is vinyl ketone.

8. The process according to claim 7 wherein said vinyl ketone is prepared by contacting said methyl ketone with formaldehyde in a molar concentration of methyl ketone to formaldehyde of about 10:1 to 2:1.

9. The process according to claim 7 wherein said methyl ketone is methyl ethyl ketone and said vinyl ketone is ethyl vinyl ketone.

10. The process according to claim 5 wherein said temperature is 180° to 650° C. and said contacting time is 2 to 15 seconds.

11. The process according to claim 5 wherein said acidic zeolite catalyst has labile metal ions exchanged with hydrogen ions at 0.1% to 100%.

12. The process according to claim 5 wherein said zeolite catalyst is selected from the group of zeolites consisting of A type, Y type, ZSM type, and SK500 type.

* * * * *

UNITED STATES PATENT AND TRADEMARK OFFICE
CERTIFICATE OF CORRECTION

PATENT NO. : 5,741,940
DATED : April 21, 1998
INVENTOR(S) : William A. Beavers

It is certified that error appears in the above-identified patent and that said Letters Patent is hereby corrected as shown below:

Column 11, line 61, delete "carbonyl" and insert therefor ---carbonyls---.

Column 11, line 64, delete "kentone" and insert therefor ---ketone---.

Column 11, line 66, delete "35" and insert therefor ---350---.

Column 12, line 16, delete "kentone" and insert therefor ---ketone---.

Column 12, line 19, delete "kentone", two occurrences, and insert therefor ---ketone---.

Column 12, line 20, delete "kentone", and insert therefor ---ketone---.

Signed and Sealed this

Twenty-fourth Day of November, 1998

Attest:

BRUCE LEHMAN

*Attesting Officer*     *Commissioner of Patents and Trademarks*